United States Patent
Olson et al.

(10) Patent No.: US 8,685,319 B2
(45) Date of Patent: Apr. 1, 2014

(54) COMBINATION OXYGENATOR AND ARTERIAL FILTER DEVICE WITH A FIBER BUNDLE OF CONTINUOUSLY WOUND HOLLOW FIBERS FOR TREATING BLOOD IN AN EXTRACORPOREAL BLOOD CIRCUIT

(75) Inventors: Robert Olson, Plymouth, MN (US); John L. Knoll, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 13/097,290

(22) Filed: Apr. 29, 2011

(65) Prior Publication Data

US 2012/0277653 A1    Nov. 1, 2012

(51) Int. Cl.
*A61M 1/00* (2006.01)
*A61M 37/00* (2006.01)

(52) U.S. Cl.
USPC .............. 422/45; 422/46; 604/6.09; 604/6.14

(58) Field of Classification Search
USPC ................ 604/4.01–6.16; 422/44–48; 29/419
See application file for complete search history.

(56) References Cited

U.S. PATENT DOCUMENTS

| | | | |
|---|---|---|---|
| 4,239,729 A | 12/1980 | Hasegawa et al. |
| 4,940,617 A | 7/1990 | Baurmeister |
| 4,975,247 A | 12/1990 | Badolato et al. |
| 5,141,031 A | 8/1992 | Baurmeister |
| 5,230,862 A | 7/1993 | Berry et al. |
| 5,462,619 A | 10/1995 | Haworth et al. |
| 5,651,765 A | 7/1997 | Haworth et al. |
| 5,762,868 A | 6/1998 | Leonard |
| 5,762,869 A | 6/1998 | White et al. |
| 5,770,149 A | 6/1998 | Raible |
| 5,782,791 A | 7/1998 | Peterson et al. |
| RE36,125 E | 3/1999 | Haworth et al. |
| 6,428,747 B1 | 8/2002 | Dueri et al. |
| 6,454,999 B1 | 9/2002 | Farhangnia et al. |
| 6,503,450 B1 | 1/2003 | Afzal et al. |
| 6,723,283 B2 | 4/2004 | Ghelli et al. |
| 6,730,267 B2 | 5/2004 | Stringer et al. |
| 6,852,280 B2 | 2/2005 | Vijay et al. |
| 6,946,099 B2 | 9/2005 | Vijay et al. |
| 6,960,322 B2 | 11/2005 | Stringer et al. |
| 6,998,093 B1 | 2/2006 | McIntosh et al. |
| 7,022,099 B2 | 4/2006 | Litzie et al. |
| 7,022,284 B2 | 4/2006 | Brian et al. |

(Continued)

OTHER PUBLICATIONS

Medtronic brochure entitled "The Affinity Hollow Fiber Oxygenator" UC9804380EN copyright 1999 (6 pages).

(Continued)

*Primary Examiner* — Philip R Wiest

(57) ABSTRACT

A combination oxygenator and arterial filter device for treating blood in an extracorporeal blood circuit. The device includes a housing maintaining a core and a fiber bundle. The fiber bundle is formed by a plurality of hollow fibers continuously helically wound about the core to form layers of level wound fibers. The layers combine to define an oxygenator region and a radially outward depth filter region. A minimum gap spacing between fibers of the oxygenator region layers is greater than a minimum gap spacing of the depth filter region layers. The fiber bundle can function as a blood oxygenator and exhibits a filtration efficiency of not less than 92% in filtering particles having a particle size of about 45 microns. An oxygenator with integrated arterial filtering capability is provided that minimally impacts the extracorporeal blood circuit prime volume.

19 Claims, 15 Drawing Sheets

(56) References Cited

U.S. PATENT DOCUMENTS

| | | |
|---|---|---|
| 7,431,754 B2 * | 10/2008 | Ogihara et al. .................. 96/8 |
| 7,476,359 B2 | 1/2009 | Maianti et al. |
| 7,749,435 B2 | 7/2010 | Ogihara et al. |
| 7,947,113 B2 | 5/2011 | Ogihara et al. |
| 2004/0219060 A1 | 11/2004 | Maianti et al. |
| 2006/0008380 A1 | 1/2006 | Moozyckine et al. |
| 2006/0089586 A1 | 4/2006 | Kaus et al. |
| 2007/0009378 A1 | 1/2007 | Blicke et al. |
| 2007/0166189 A1 | 7/2007 | Ogihara |
| 2007/0166190 A1 | 7/2007 | Ogihara et al. |
| 2007/0231203 A1 | 10/2007 | Mizoguchi et al. |
| 2008/0060990 A1 | 3/2008 | Bernard et al. |
| 2008/0199357 A1 | 8/2008 | Gellman et al. |
| 2009/0087342 A1 | 4/2009 | Maianti et al. |
| 2009/0137939 A1 | 5/2009 | Maianti et al. |
| 2009/0230058 A1 | 9/2009 | Boris-Moeller |
| 2010/0224559 A1 | 9/2010 | Ogihara et al. |
| 2010/0274170 A1 * | 10/2010 | Carpenter et al. ........... 604/6.09 |

OTHER PUBLICATIONS

Medtronic brochure entitled "Affinity NT Oxygenation Systems" UC200000683EN copyright 1999 (6 pages).

* cited by examiner

COMBINATION OXYGENATOR AND ARTERIAL FILTER DEVICE WITH A FIBER BUNDLE OF CONTINUOUSLY WOUND HOLLOW FIBERS FOR TREATING BLOOD IN AN EXTRACORPOREAL BLOOD CIRCUIT

BACKGROUND

The present disclosure relates to extracorporeal blood circuits, systems, and methods of use. More particularly, it relates to devices for oxygenating and filtering blood in an extracorporeal blood circuit, and methods of making such devices.

An extracorporeal blood circuit is commonly used during cardiopulmonary bypass to withdraw blood from the venous portion of the patient's circulation system (via a venous cannula) and return the blood to the arterial portion (via an arterial cannula). The extracorporeal blood circuit generally includes a venous drainage or return line, a venous blood reservoir, a blood pump, an oxygenator, an arterial filter, and blood transporting tubing, ports, and connection pieces interconnecting the components. As shown in FIG. 1, some prior art extracorporeal blood circuits drain venous blood from patient 10 via a venous return line 12. Cardiotomy blood and surgical field debris are aspirated from the patient 10 by a suction device 16 that is pumped by a cardiotomy pump 18 into a cardiotomy reservoir 20. Venous blood from the venous return line 12, as well as de-foamed and filtered cardiotomy blood from the cardiotomy reservoir 20, are discharged into a venous blood reservoir 22. Air entrapped in the venous blood rises to the surface of the blood in the venous blood reservoir 22 and is vented to atmosphere through a purge line 24. A venous blood pump 26 draws blood from the venous blood reservoir 22 and pumps it through an oxygenator 28 and an arterial blood filter 29. An arterial line 14 returns the oxygenated and filtered blood back to the patient's arterial system via an arterial cannula (not shown) coupled to the arterial line 14.

The oxygenator component of the extracorporeal blood circuit is well known. In general terms, the oxygenator takes over, either partially or completely, the normal gas exchange function of the patient's lungs. In oxygenators that employ a microporous membrane, blood is taken from the patient and is circulated through the oxygenator on one side of the membrane. Concurrently, an oxygenating gas is passed through the oxygenator on the other side of the membrane. Carbon dioxide diffuses from the blood across the microporous membrane into the passing stream of oxygenating gas; at the same time, oxygen diffuses from the oxygenating gas across the membrane into the blood. The circulating blood, having thereby been reduced in carbon dioxide content and enriched in oxygen, is returned to the patient. One popular type of membrane oxygenator is referred to as a hollow fiber oxygenator, and is illustrated generally in U.S. Pat. No. 4,239,729. A hollow fiber oxygenator employs a large plurality (typically tens of thousands) of microporous or semipermeable hollow fibers disposed within a housing. These hollow fibers are sealed in end walls of the housing that are then fitted with skirted end caps. One end cap is fitted with an inlet, the other end cap is fitted with an outlet. A peripheral wall of the housing has an inlet located interiorly of one of the end walls and an outlet located interiorly of the other end wall. The oxygenating gas enters the device through the inlet, passes through the lumens of the hollow fibers, and exits the device through the outlet. It will be understood that carbon dioxide diffuses from the blood flowing over the outer surfaces of the hollow fibers through the fiber walls and into the stream of oxygenating gas. At the same time, oxygen from the oxygenating gas flowing through the lumens of the hollow fibers diffuses through the fiber walls and into the blood flowing about the fibers to oxygenate the blood.

A well-accepted technique for forming a hollow fiber oxygenator is to spirally wind ribbons of the fibers about an internal supporting core, as described for example in U.S. Pat. No. 4,975,247. Blood flow through the resultant annular "bundle" of fibers can be in various directions such as radially outward, axial, circumferential, etc. With radially outward flow designs, U.S. Pat. No. 5,462,619 describes an improved winding technique that provides desired pressure drops and minimal clotting risks by a graduated packing fraction. An oxygenator product available from Medtronic, Inc., under the trade name Affinity® NT Oxygenator, is one example of a spirally wound hollow fiber oxygenator with graduated packing fraction.

For purposes of this disclosure, packing fraction is defined to mean the fraction of a unit volume of bundle space occupied by fibers (or filaments). The packing fraction may be determined in ways known in the art, including the convenient method of measuring the interstitial space between fibers (or filaments) by weight gain when a unit volume is primed with a known liquid. Packing fraction at a particular region or zone located radially outward may be determined by stopping the corresponding winding process at the radially inner radial boundary of the region or zone and determining the packing fraction at that stage, and then continuing the winding process to the outer radial boundary of the region or zone and determining the packing fraction at that stage. Computations known in the art will determine the packing fraction of the region or zone using the prior two values.

Arterial filters are also well known, and can take various forms appropriate for air handling and blood filtration. In general terms, the conventional arterial filter device includes one or more screen-type filters within a filter housing that combine to capture and remove particulate (e.g., emboli) on the order of about 20-40 microns and larger, as well as to trap gaseous microemboli larger than a certain size to prevent the emboli from reaching the patient. These emboli can cause significant harm to the patient by plugging small arteries, arterioles, and or capillaries, preventing adequate blood flow to small or large areas of tissue or organs. Examples of known arterial blood filters are described in U.S. Pat. Nos. 5,651,765 and 5,782,791. Arterial blood filters are also available from Medtronic, Inc. under the trade name Affinity® Arterial Filter.

Conventionally, the arterial filter device is fluidly connected within the extracorporeal circuit downstream (or upstream) of the oxygenator device by tubing. While implementation of the separate oxygenator and arterial filter devices as part of an extracorporeal blood circuit is well accepted, certain concerns arise. An arterial filter typically adds 200 ml (or more) of prime volume to the extracorporeal blood circuit; this added prime volume is undesirable as it can lead to increased hemodilution of the patient. As a point of reference, the volume of blood and/or prime solution liquid that is pumped into the extracorporeal blood circuit to "prime" the circuit is referred to as the "prime volume". Typically, the extracorporeal blood circuit is first flushed with $CO_2$ prior to priming. The priming flushes out any extraneous $CO_2$ gas from the extracorporeal blood circuit prior to the introduction of the blood. The larger the prime volume, the greater the amount of prime solution present in the extracorporeal blood circuit that mixes with the patient's blood. The mixing of the blood and prime solution causes hemodilution that is disadvantageous and undesirable because the relative concentration of red blood cells must be maintained during the surgical procedure in order to minimize adverse effects to the patient. It is therefore desirable to minimize the extracorporeal blood circuit's prime volume (and thus the required volume of prime solution).

In light of the above, a need exists for an extracorporeal blood circuit device that provides oxygenation and arterial filtering properties at least commensurate with conventional oxygenator and arterial filter components, yet minimizes the overall impact on the prime volume of the extracorporeal blood circuit.

SUMMARY

Some aspects of the present disclosure relate to a combination oxygenator and arterial filter device for treating blood in an extracorporeal circuit. The device includes a housing, a core, and a fiber bundle. The core is maintained within the housing and defines a central longitudinal axis. The fiber bundle is disposed within the housing and is formed by a plurality of microporous hollow fibers continuously wound about the core to generate a plurality of layers. Each layer is composed of level wound fibers, with each successive layer being radially outward of an immediately preceding layer relative to the central longitudinal axis. The layers combine to define an oxygenator region and a depth filter region. The depth filter region is radially outward of the oxygenator region. A minimum gap spacing between axially adjacent fibers of the oxygenator region layers is greater than a minimum gap spacing between axially adjacent fibers of the depth filter region layers. In addition to providing desired oxygenation properties appropriate for oxygenating blood as part of an extracorporeal blood circuit, the fiber bundle exhibits a filtration efficiency akin to an arterial filter. The fiber bundle has a filtration efficiency of not less than 92%, alternatively not less than 95%, in filtering particles having a particle size of about 45 microns. In other embodiments, the fiber bundle has a filtration efficiency of not less than 94%, alternatively not less than 97%, in filtering particles having a particle size of about 65 microns. In other embodiments, the fiber bundle has a filtration efficiency of not less than 55%, alternatively not less than 60%, in filtering particles having a particle size of about 20 microns. With any of these constructions, an oxygenator with integrated arterial filter capability is provided having reduced foreign surface area and reduced impact on the prime volume of the corresponding extracorporeal blood circuit (e.g., on the order of 25 ml of less) as compared to conventional blood circuit arrangements utilizing physically separate oxygenator and arterial filter components.

Yet other aspects of the present disclosure relate to an extracorporeal blood circuit including a venous line, an arterial line, and a combination oxygenator and arterial filter device. The device forms an inlet side and an outlet side. The inlet side is fluidly connected to the venous line, that in turn is arranged to receive blood from a patient (e.g., via a pump). Conversely, the outlet side is fluidly connected to the arterial line that in turn is located to deliver treated blood to the patient. The combined oxygenator and arterial filter device includes the fiber bundle as described above. In some embodiments, the extracorporeal blood circuit is characterized by the absence of an additional arterial filter between the combination device and the arterial line.

Yet other aspects of the present disclosure related to a method of making a combination oxygenator and arterial filter device for treating blood in an extracorporeal blood circuit. The method includes helically winding a plurality of hollow microporous fibers about an internal core to define a fiber bundle having a plurality of layers, each layer being composed of level wound fibers and each successive layer being radially outward of an immediately preceding layer relative to a central longitudinal axis of the core. The layers of the fiber bundle combine to define an oxygenator region and a depth filter region, the depth filter region being radially outward of the oxygenator region. A minimum gap spacing between axially adjacent fibers of the oxygenator region layers is greater than a minimum gap spacing between axially adjacent fibers of the depth filter region layers. The fiber bundle exhibits a filtration efficiency of not less than 92% in filtering particles having a particle size of about 45 microns. Finally, the fiber bundle is disposed within a housing.

DETAILED DESCRIPTION

Figure 1:
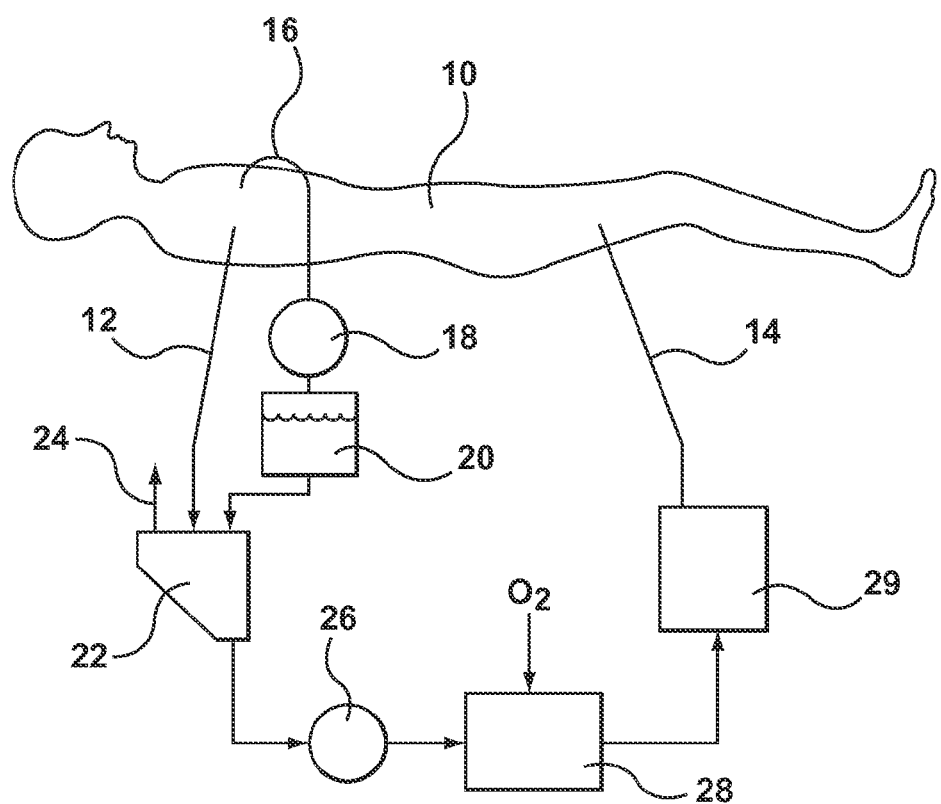
FIG. 1 is a schematic diagram of a prior art extracorporeal blood circuit including separated oxygenator and arterial filter devices.
Figure 2A:
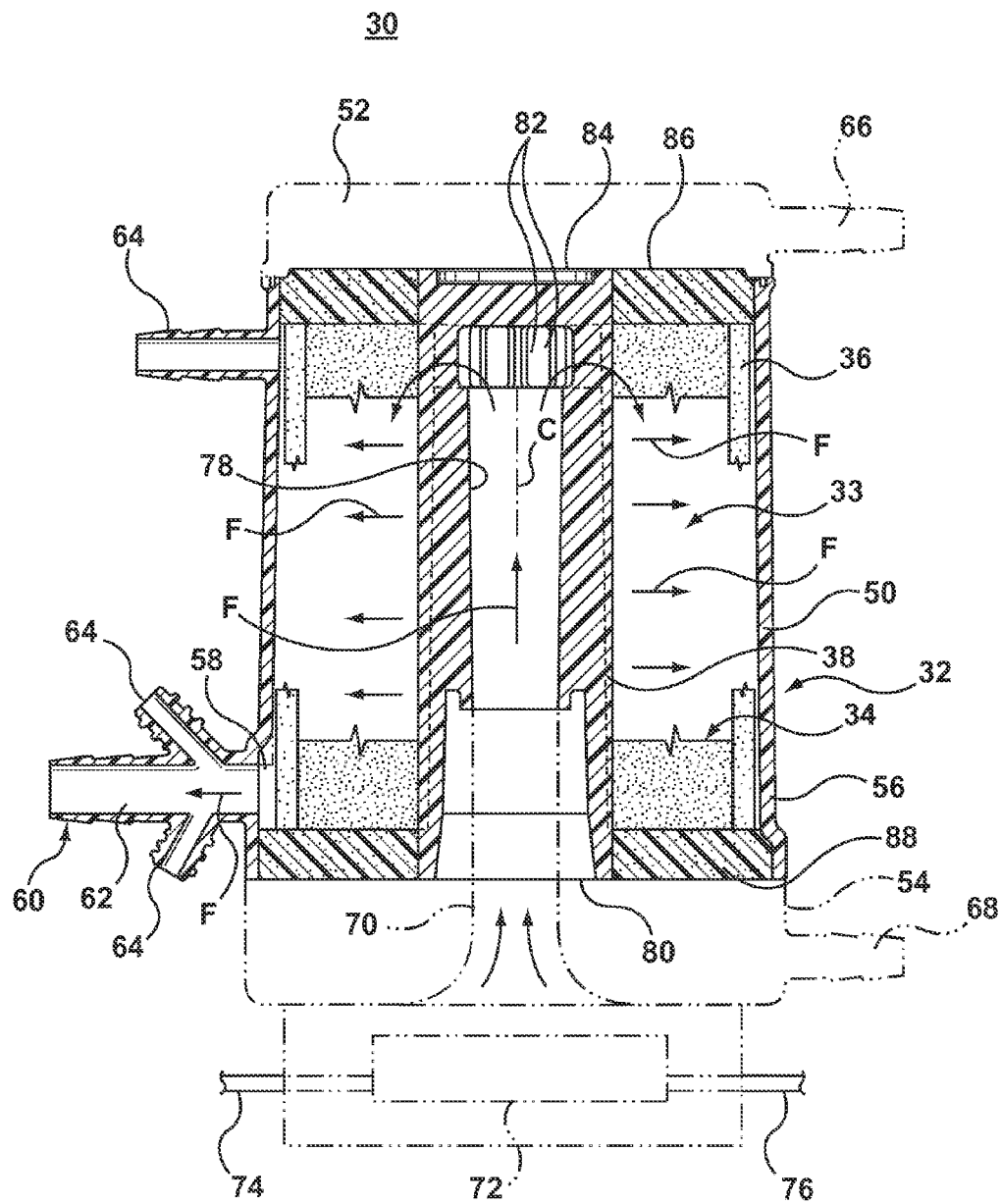
FIG. 2A is a cross-sectional view of a combination oxygenator and arterial filter device in accordance with principles of the present disclosure, depicting the device vertically oriented as it would be in use.

One embodiment of a combination blood oxygenator and arterial filter device 30 in accordance with principles of the present disclosure is shown in FIG. 2A. The device 30 includes a housing 32 and a fiber bundle 33 forming an oxygenator region 34 (referenced generally) and an arterial depth filter 36 region (referenced generally). Details on the various components are provided below. In general terms, however, the fiber bundle 33 is disposed within the housing 32 about an internal core 38, with the oxygenator region 34 being radially inward of the depth filter region 36 (relative to a longitudinal axis of the core 38). A blood flow path is defined by the housing 32, directing blood flow radially through the oxygenator region 34 and then the depth filter 36, with the oxygenator region 34 primarily facilitating oxygenation of the supplied venous blood, and the depth filter region 36 primarily removing gaseous and particulate microemboli. In some constructions, some oxygenation can further occur across the depth filter region 36 and/or some gaseous and particulate microemboli filtration can occur across the oxygenator region 34. The device 30 is thus amenable for insertion within an extracorporeal blood circuit as described below, providing necessary oxygenation and filtration capabilities with minimal overall impact on the extracorporeal circuit's prime volume.

The housing 32 can assume various forms, and generally includes or defines an outer wall 50, a gas header or cap 52, and a bottom header or cap 54. The outer wall 50 is sized to contain the fiber bundle 31, and can be generally cylindrical. At a base region 56, an optional annular eccentric relieved area 58 forms, or is fluidly connected to, an outlet manifold 60 having a blood outlet 62. Other optional outlets or ports, such as sample or recirculation ports 64, can be provided by the manifold 60 or may be suitably located elsewhere along the outer wall 50.

The gas header 52 is configured for assembly to the outer wall 50, and includes or defines a gas inlet 66. Similarly, the bottom header 54 is configured for assembly to the outer wall 50 opposite the gas header 52, and can form or include a gas outlet 68. The bottom header 54 also includes or defines a blood entrance or inlet 70 for directing a blood flow into the device 30.

Figure 2B:
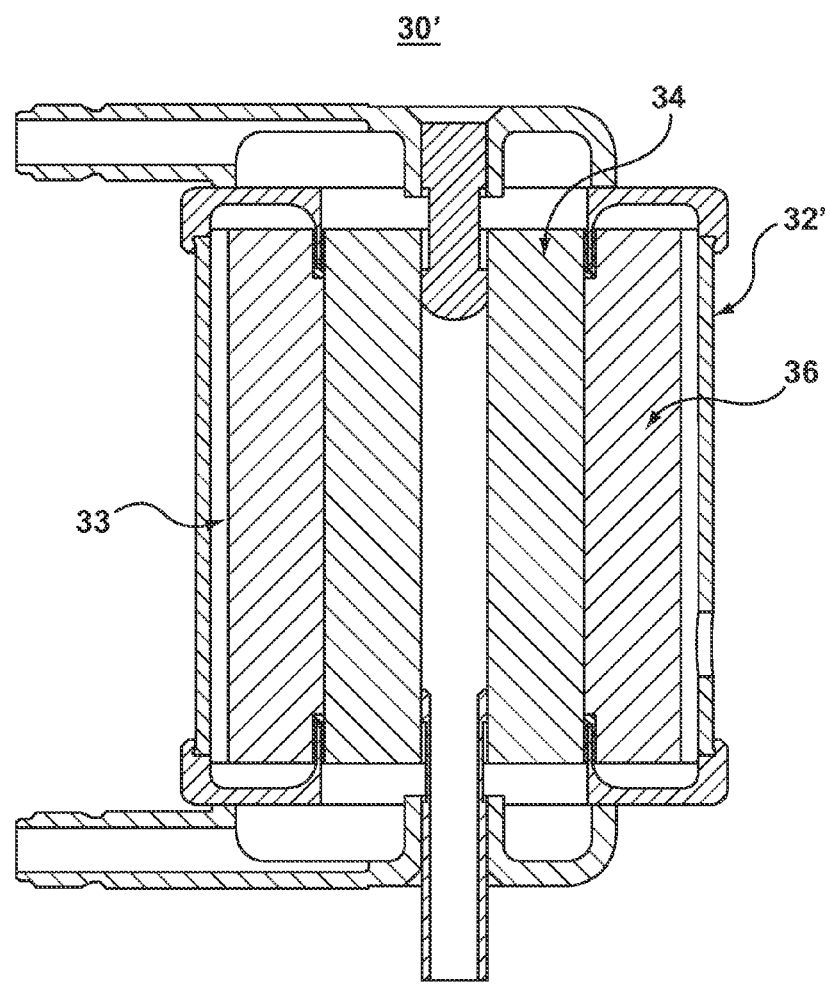
FIG. 2B is a cross-sectional view of another combination oxygenator and arterial filter device in accordance with principles of the present disclosure.
Figure 2C:
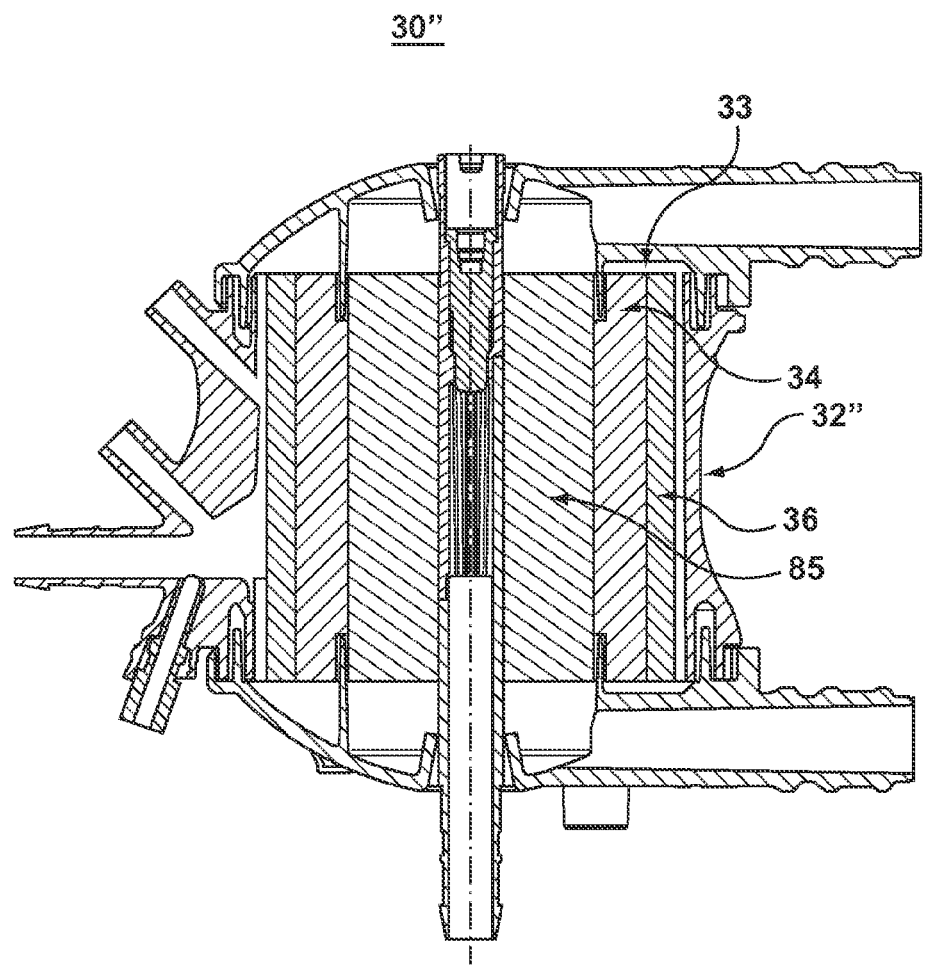
FIG. 2C is a cross-sectional view of another combination oxygenator and arterial filter device in accordance with principles of the present disclosure.

The device 30, at the bottom header 54, can optionally be provided with, or carry, a suitable heat exchanger 72. A fluid type heat exchanger 72 is depicted with a heat exchange fluid inlet 74 and a heat exchange fluid outlet 76, but other suitable heat exchange devices can be incorporated with the device 30, for example an electrical heating and cooling device might be used. In other embodiments, the heat exchanger 72 is omitted. For example, FIG. 2B illustrates an alternative device 30' in accordance with principles of the present disclosure and including the oxygenator region 34 and the arterial depth filter region 36 within a housing 32'. The device 30' does not include a heat exchanger. Conversely, FIG. 2C illustrates another device 30" in accordance with the principles of the present disclosure and including the oxygenator region 34 and the arterial depth filter 36 within a housing 32". Further, a bundled heat exchanger 85 is disposed between the fiber bundle 33 and the core 38.

Figure 2D:
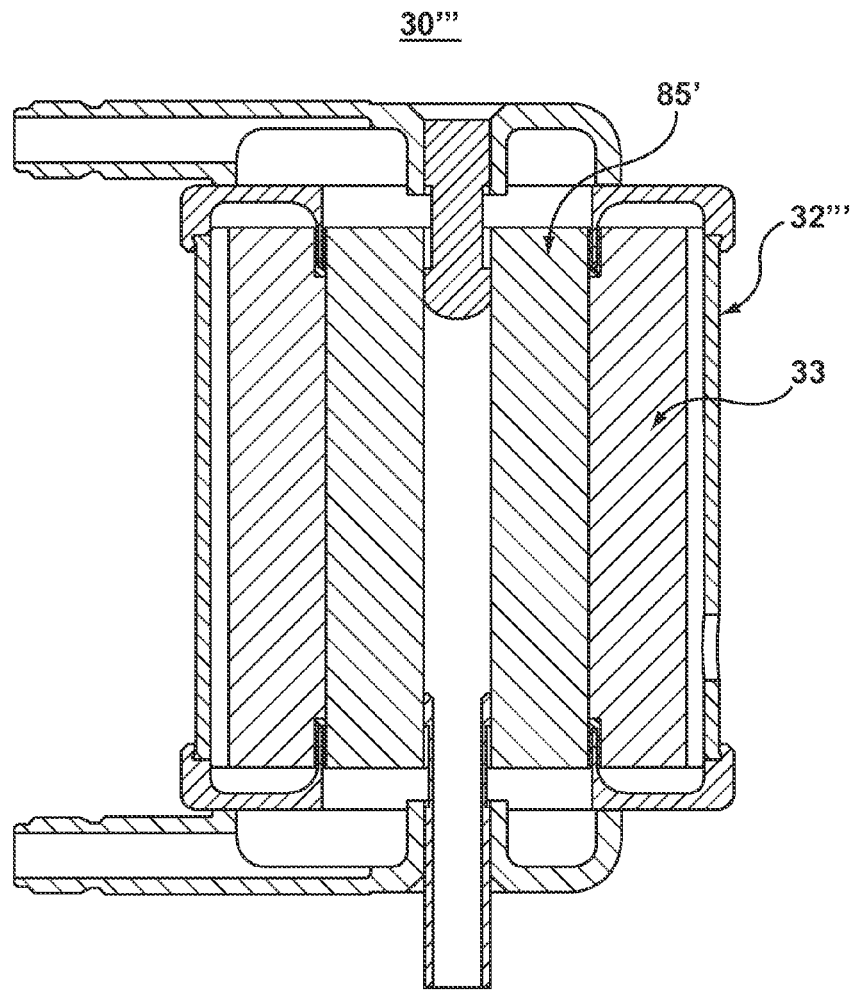
FIG. 2D is a cross-sectional view of another combination oxygenator and arterial filter device further including a heat exchanger in accordance with principles of the present disclosure.

FIG. 2D illustrates another device 30''' in accordance with principles of the present disclosure and includes the fiber bundle 33 placed over a bundled heat exchanger 85' and disposed within a housing 32'''. In some embodiments, the fiber bundle 33 has an inner diameter of approximately 2.0 inch (+/−0.1 inch) and an outer diameter of approximately 3.5 inch (+/−0.1 inch).

Returning to FIG. 2A and as mentioned above, the fiber bundle 33 is formed about the internal core 38. The internal core 38 is a generally cylindrical, hollow body, and is configured for winding of (and supporting) the fiber bundle 31 about an outer surface thereof. The internal core 38 can optionally incorporate various features (e.g., ribs, flanges, recessed regions, etc.) that promote robust assembly with the fiber bundle 33. Regardless, the internal core 38 forms a central passage 78 that is fluidly open to the blood inlet 70 at a first end 80. A chamber 82 is formed adjacent a second end 84 of the core 38, and is fluidly open to an exterior of the internal core 38 by one or more windows (not shown) that dictate a radially outward blood flow path from the passage 78 as reflected by arrows in FIG. 2A.

The fiber bundle 33 is an annular bundle of helically-wound, microporous hollow fibers (drawn generally in FIG. 2A, but identified in greater detail below with reference to FIGS. 3A-3C) positioned along the internal core 38. As made clear below, the wound hollow fibers form layers relative to which the oxygenator region 34 and the depth filter region 36 are theoretically generated. The top and bottom ends of the fiber bundle 33, at least along the oxygenator region 34 and in some embodiments along an entirety of the oxygenator and depth filter regions 34, 36, are embedded in solidified potting compositions 86, 88 at top and bottom ends, respectively, of the housing 32. The fiber lumens communicate with the outer surface of the upper and lower potted compositions 86, 88, respectively. An oxygenating gas introduced via the gas inlet 66 flows into the gas header 52, through the lumens of the hollow fibers (at least along the oxygenator region 34), down to the opposite ends of the hollow fibers at the lower potted region 88, and into the gas outlet passage 68.

It should be understood that the potting process referred to herein above is a well known fiber potting process in which a potting material (e.g., polyurethane) is introduced by centrifuging and reacted in situ. Other appropriate potting materials may be used. Suitable sealants and gaskets may be used at joints in the housing 32, such as the joints between the top and bottom headers 52, 54 and the outer wall 50. Any suitable microporous fiber may be used in the fiber bundle 33; for example, a suitable fiber is the microporous polypropylene fiber available under the trade name CELGARD™ X30 (outer diameter on the order of 200-300 microns) from Membrana of Charlotte, N.C.

The fiber bundle 33 extends radially outward relative to a central longitudinal axis C of the internal, core 38. The fibers can include a first plurality of fibers positioned (e.g., wound) helically around the internal core 38 in a first direction from the first end 80 to the second end 84 of the internal core 38, and a second plurality of fibers positioned helically around the internal core 38 in a second direction opposite the first direction, and thus from the second end 84 to the first end 80. Regardless, in some embodiments, the microporous fibers of the fiber bundle 33 are continuously wound to define both of the regions 34, 36 such that a physical or visible demarcation between the regions 34, 36 is not present (thus, the visual difference embodied by FIGS. 2A-2C between the regions 34, 36 does not exist). For purposes of better understanding some features of the present disclosure, it may be helpful to view the oxygenator region 34 and the depth filter region 36 as being physically distinct from one another as in the following descriptions. With embodiments in which the oxygenator region 34 and the depth filter region 36 are commonly formed by a continuous winding of the same fibers, the oxygenator region 34 can perform some of the filtration features described below with respect to the depth filter region 36; with these same constructions and where the fiber lumens of the depth filter region 36 are fluidly connected to the gas inlet and outlet, the depth filter region 36 can perform some of the oxygenation features described herein with respect to the oxygenator region 34. Various acceptable methods of winding the microporous fibers about the internal core 38 to generate the oxygenator region 34 are described in U.S. Pat. Nos. 4,975,247 and 5,462,619, the entire teachings of both of which are incorporated herein by reference. For example, as described in the '619 patent, the oxygenator region 34 can be wound to define a graduated packing fraction that increases from an inside radius of the oxygenator bundle 40 to the outside radius.

Figure 3A:
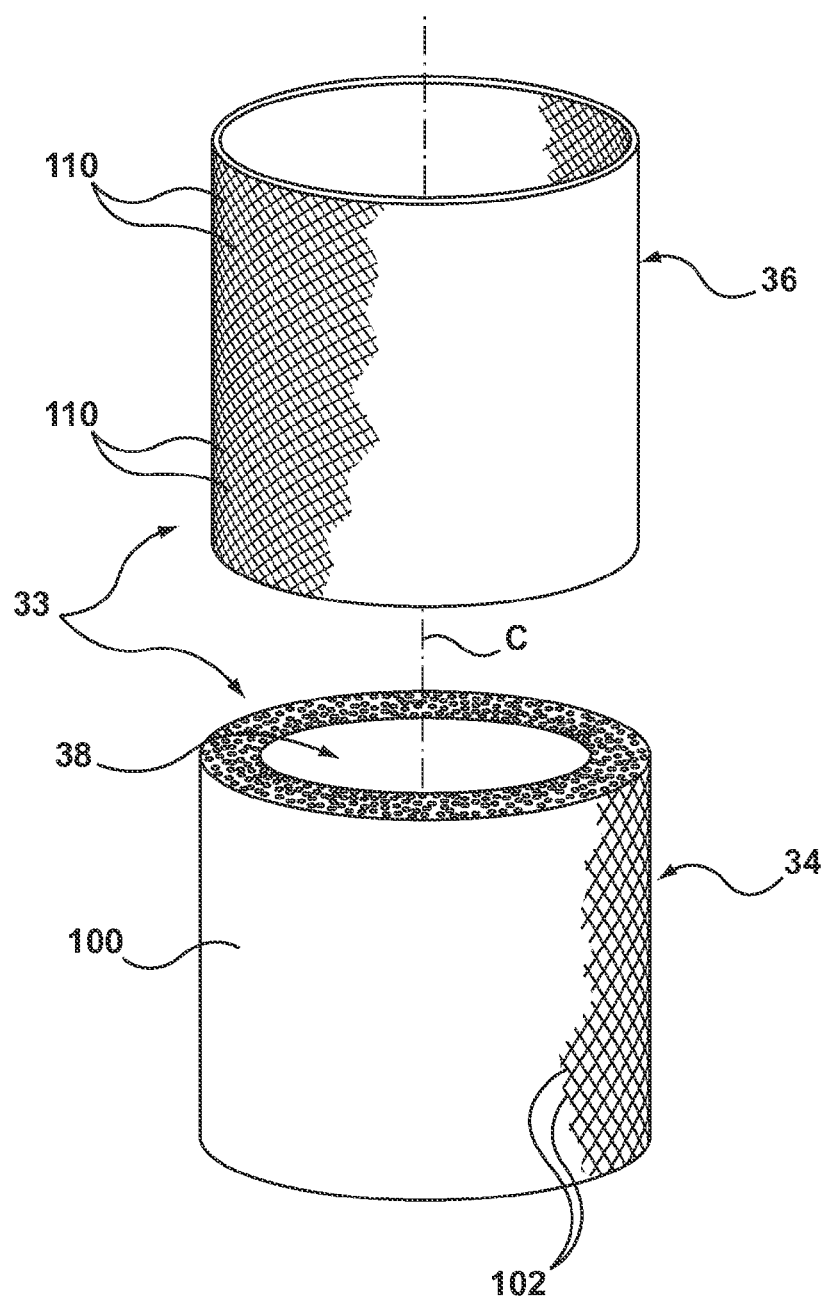
FIG. 3A is a perspective, exploded view of a filter bundle component of the devices of FIGS. 2A-2D.
Figure 3B:
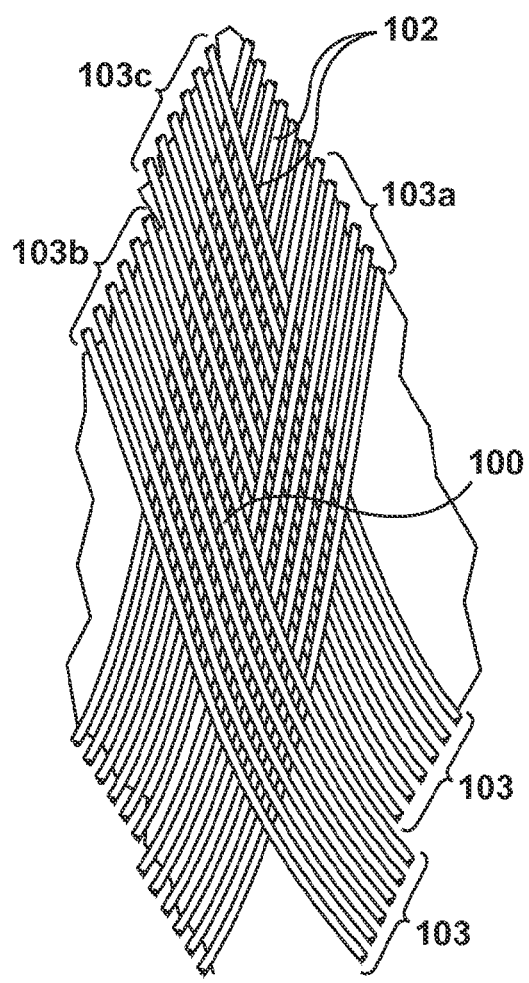
FIG. 3B is a simplified, greatly magnified top plan view of a portion of an oxygenator region of the fiber bundle of FIG. 3A.
Figure 3C:
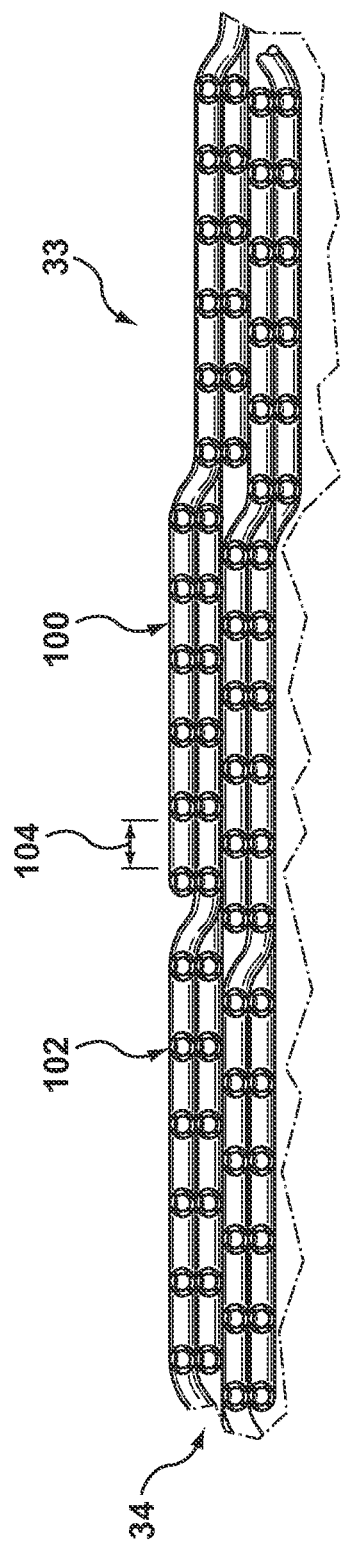
FIG. 3C is a cross-sectional, greatly magnified view of a portion of an oxygenator region of the fiber bundle of FIG. 3A.

Regardless of the packing fraction properties of the oxygenator region 34, an oxygenator exterior face 100 is hypothetically generated during the winding process, as shown in FIG. 3A. The oxygenator exterior face 100 is defined as the terminal face of the oxygenator region 34 opposite the internal core 38 (omitted from the view of FIG. 3A for ease of explanation, but a location of which relative to the oxygenator region 34 being generally indicated). The oxygenator exterior face 100 is generally annular, and is comprised of a series of axially or longitudinally adjacent windings of the hollow fibers 102 (a thickness or diameter of which is exaggerated in FIG. 3A for ease of explanation). Commensurate with the above descriptions, individual ones of the hollow fibers 102 may be arranged in differing wind directions along the oxygenator exterior face 100. Further, in some embodiments, selected groupings of the hollow fibers 102 may be collectively cross-wound in identical directions as a fiber ribbon (e.g., as described in the '619 patent, six continuous hollow fibers are collectively cross-wound as a discernable ribbon). As such, not all of the fibers 102 along the oxygenator exterior face 100 may be precisely axially aligned. For example, FIG. 3B depicts a ribbon 103 of the fibers 102 being collectively cross-wound, with exposed segments 103a, 103b, 103c of the wound fiber ribbon 103 each forming a portion of the oxygenator exterior face 100. However, and as reflected in FIG. 3C, a minimum gap spacing 104 is established between axially adjacent ones of the fibers 102, with the minimum gap spacing 104 being in the range of 20-70 microns in some embodiments, in the range of 30-60 microns in other embodiments, and on the order of 38 microns in other embodiments.

Returning to FIG. 3A, the depth filter region 36 is constructed to be directly applied or formed over the oxygenator region 34 (e.g., a continuation of the oxygenator region 34 fiber winding) as described below, and is generally characterized as a radially outward extension from the oxygenator exterior face 100. In particular, the depth filter region 36 includes a plurality of fibers or filaments 110 (referenced generally) arranged over the oxygenator exterior face 100. As mentioned above, in some embodiments, the fibers 102 defining the oxygenator region 34 are continuously wound to further define the depth filter region 36. With this in mind, the depth filter fibers 110 can be made from a plastic resin such as polyester, polypropylene, polyethylene, etc., and are microporous hollow fibers. The fibers 110 may or may not be identical in terms of material, structure, or size, but in some embodiments a maximum outer diameter of the filter region fibers 110 is on the order of 200-300 microns. In other embodiments, the filter region fibers 110 have a maximum outer diameter not greater than about 200 microns; in other embodiments not greater than 150 microns. In yet other embodiments, an outer diameter of the filter region fibers 110 is in the range of 40-50 microns.

Figure 4A:
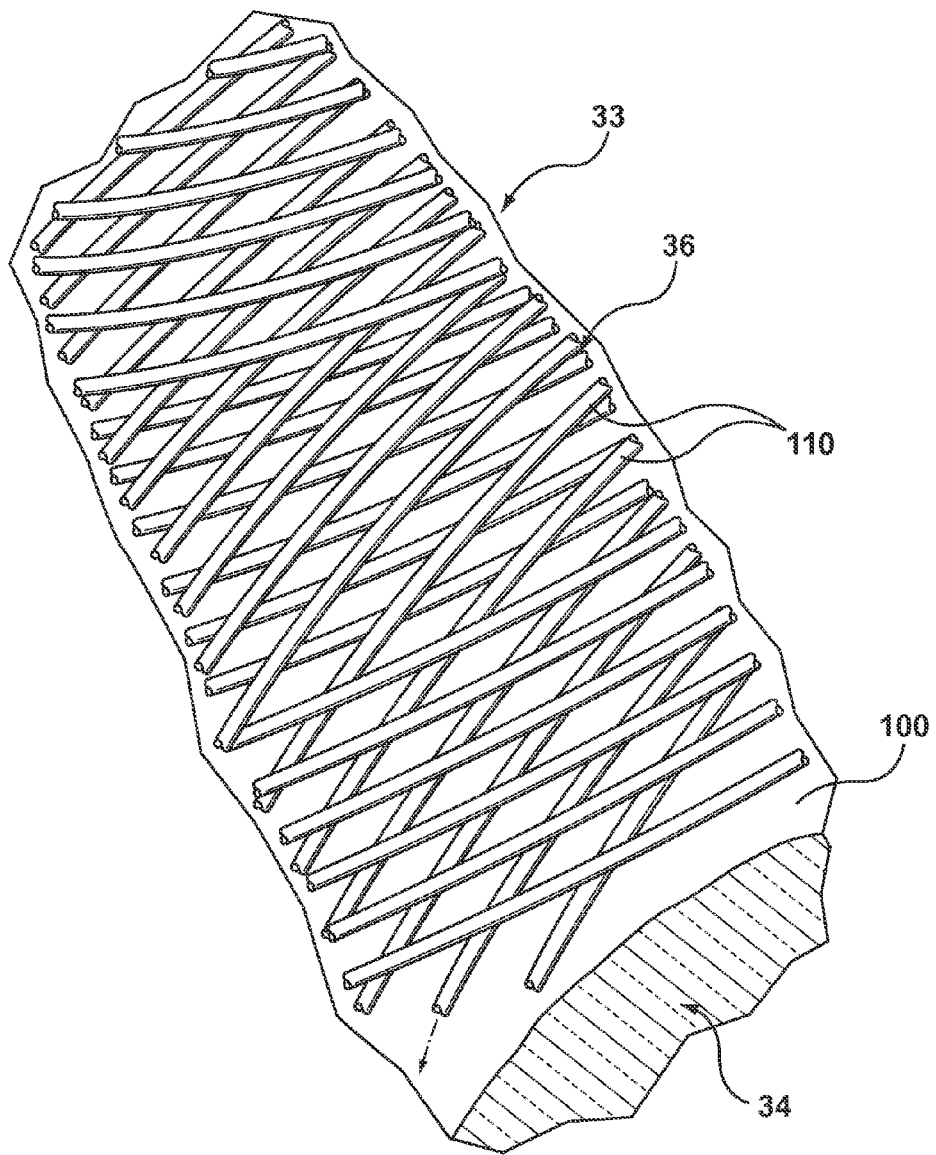
FIG. 4A is a perspective, greatly magnified view of a portion of the fiber bundle of FIG. 3A illustrating a portion of a depth filter region applied to the oxygenator region.
Figure 4B:
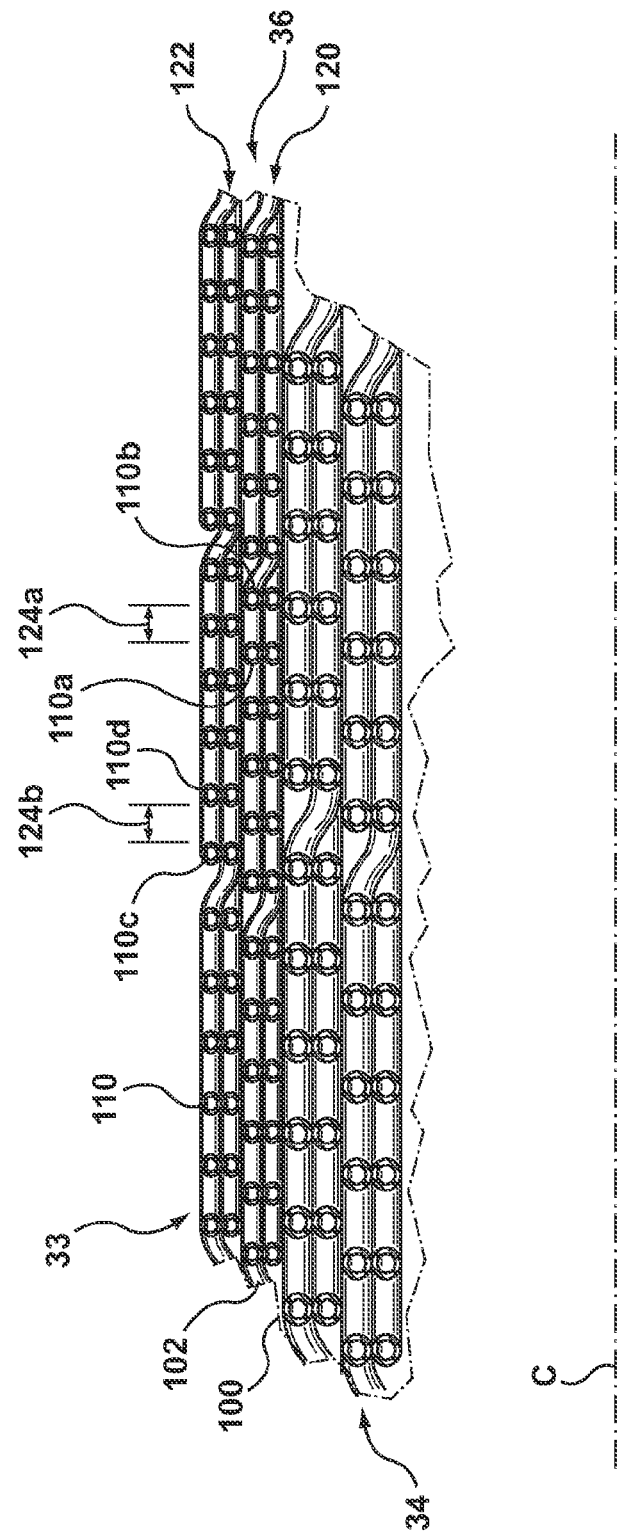
FIG. 4B is a cross-sectional, greatly magnified view of a portion of the depth filter region of FIG. 4A.

Regardless of an exact construction and/or materials of the filaments region fibers 110, the fibers 110 are arranged over the oxygenator exterior face 100 so as to define filter layers of level cross-wound fibers as shown in FIG. 4A (the oxygenator region 34 and the oxygenator exterior face 100 shown schematically in FIG. 4A for ease of illustration). In FIG. 4B, the depth filter region 36 has at least a first filter layer 120 of level wound fibers, optionally a second filter layer 122 of level wound fibers, and possibly additional filter layers (not shown) of level wound fibers on the second layer 122. The layers 120, 122 are annular, arranged about the central axis C described above, with various ones of the depth filter region fibers 110 extending spirally around the central axis C. In some embodiments, the fibers 110 extend in differing directions along each of the layers 120, 122 such that each of the layers 120, 122 is composed of level cross-wound fibers. Alternatively, the fibers in one or both of the layers 120, 122 can be level wound without cross-winding. With the construction of FIGS. 4A and 4B, the layers 120, 122 can be characterized as cross-level wound or plan level composite wound filter layers 120, 122.

A minimum gap spacing 124 is established between axially or longitudinally adjacent ones of the depth filter region fibers 110 within each of the first and second layers 120, 122. The phrases "axially adjacent" and "longitudinally adjacent" as used in this disclosure are in reference to two filaments (or fibers) immediately above or below one another and having aligned center points that intersect in a plane parallel to the central axis C. Thus, relative to the first filter layer 120, axially or longitudinally adjacent fibers 110a, 110b establish the minimum gap spacing identified at 124a; similarly, the fibers 110c, 110d of the second filter layer 122 establish the minimum gap spacing identified at 124b. It will be understood that with certain manufacturing techniques envisioned by the present disclosure, in some regions of the depth filter region 36, a larger gap may exist between axially adjacent fibers 110. By minimizing a size of the minimum gap spacings 124 (e.g., on the order of 40 microns), radial blood flow through the filter layers 120, 122 provides enhanced filtration efficiency for a given size of microemboli. Although the depth filter region 36 has been described as having two of the filter layers 120, 122, in other embodiments, three or four or more of the layers of level wound fibers can be formed by the fibers 110, with each successive layer being radially outward of the previous layer. Regardless, and as reflected in FIG. 4B, the first filter layer 120 is formed directly on the oxygenator exterior face 100 such that the fibers 110 of the first layer 120 physically contact (and are optionally continuous of) the oxygenator fibers 102 of the oxygenator exterior face 100.

Figure 5:
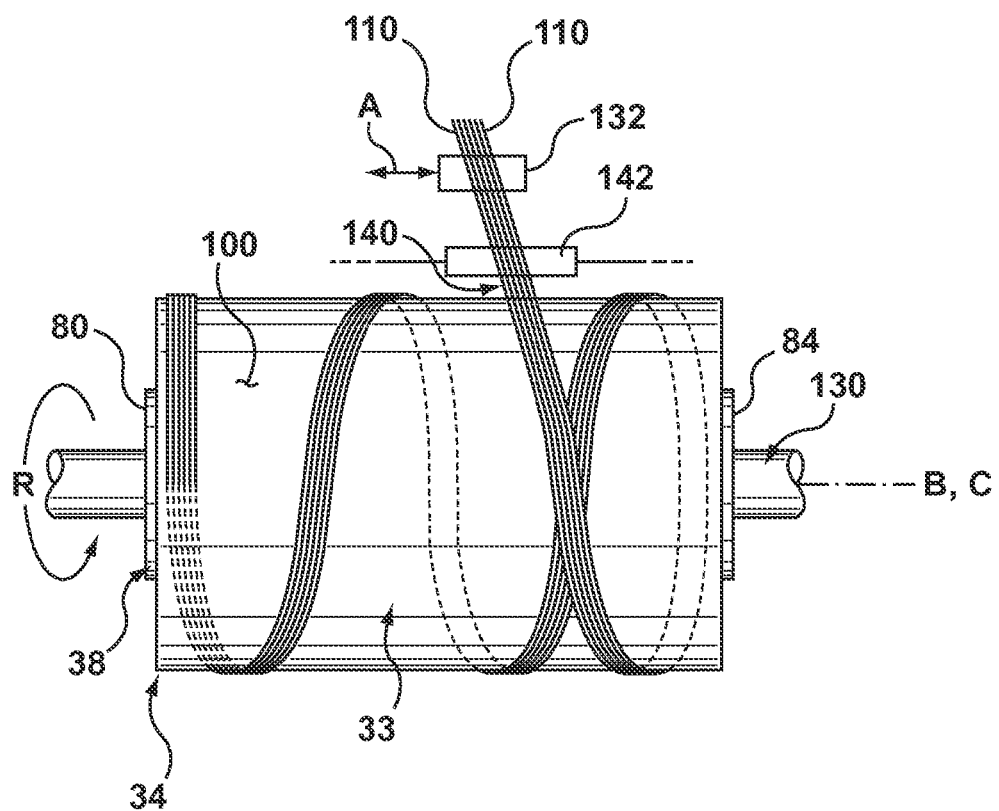
FIG. 5 is a simplified side view of a winding apparatus forming the fiber bundle of FIG. 3A in accordance with principles of the present disclosure.

In some embodiments, the fibers 110 are applied to the oxygenator exterior face 100 via a winding operation. The fiber winding process may be conveniently performed on an apparatus of the type illustrated schematically in FIG. 5 that optionally may also be employed for winding the oxygenator region 34 onto the internal core 38. In general terms, the fiber winding apparatus comprises a rotating mounting member 130 and a guide head 132. The rotating mounting member 130 rotatably maintains the internal core 38 (referenced generally), and thus the previously-formed oxygenator region 34 (the exterior face 100 of which is partially visible and drawn schematically in FIG. 5 for ease of explanation). The guide head 132 is arranged to travel reciprocally as illustrated by a double-headed arrow line A in FIG. 5 with respect to a longitudinal axis B of the mounting member 130 (i.e., the line of travel A of the guide 132 is parallel to the axis of rotation B of the mounting member 130).

As described, for example, in U.S. Pat. No. 4,975,247, the guide head 132 maintains a number of fiber guides (e.g., tubes, holes, pins, etc.) through which the fibers 110 are threaded as they enter the guide head 132 from a supply container (not shown). Upstanding ribs, grooves, guide pins, tubes, etc., may be used to space the fibers 110 at the guide head 132. Commercially available winding apparatus are available for wrapping the continuous fibers 102, 110. For example, Entec of Salt Lake City, Utah offers a winding apparatus with electronic gearing for varying the rotational speed of the mounting member 130 and the traverse speed of the guide head 132 during winding. The internal core 38 is mounted on the mounting member 130, with central axis C of the core 38 thus aligned with the axis of rotation B. The guide head 132 is then positioned at the left hand side (as viewed in FIG. 5) of the oxygenator region 34. A ribbon 140 of continuous fibers 110 (e.g., six of the fibers 110) is threaded through the fiber guides of the guide head 132. The leading end of the fiber ribbon 140 is affixed to the oxygenator exterior face 100 extended at the far left end thereof. Rotation of the mounting member 130 is begun in the direction indicated by arrow R in FIG. 5. Motion of the guide head 132 is synchronized with rotation of the mounting member 130, and automatically travels axially of the oxygenator region 34 as the mounting member 130 rotates. It will be recognized by those skilled in the art that the guide head 132 travels axially a fixed distance for each revolution of the mounting member 130.

The guide head 132 travels from the first end 80 (left hand side of FIG. 5) of the internal core 38 to the second end 84 (right hand side of FIG. 5) where it decelerates. After decelerating, the guide head 132 reverses direction, accelerates and travels back to its starting position. After decelerating again and reversing direction, the guide head 132 begins its travel cycle anew. Alternatively, the guide head 132 may stop and dwell at the end points of the traverse. The reciprocal travel for the guide head 132 and the concurrent rotation of the mounting member 130 on which the core 38 has been mounted is continued until a depth filter bundle region of desired diameter has been wound onto the oxygenator region 34, with the back-and-forth cycling of the guide head 132/ribbon 140 creating the layers of level cross-wound fibers described above.

As explained more fully at column 10, line 23 through column 11, line 62 of the '247 patent, in the left-to-right travel of the guide head 132, the fiber ribbon 140 is wound spirally around the oxygenated bundle 40, and the individual fibers 110 in the ribbon 140 are laid down in contact with the oxygenator exterior face 100. In the subsequent second traverse (right-to-left in FIG. 5) of the guide head 132, the fiber ribbon 140 continues to be spirally wound onto the oxygenator region 34. Portions of the fibers 110 laid down during the second traverse of the guide head 132 contact previously-applied fiber 110 at certain crossover points. Except for these crossover points at which there is fiber-to-fiber contact with the fibers 110 laid down during the first traverse of the guide head 132, the fibers 110 laid down during the second traverse of the guide head 132 come into direct contact with the oxygenator exterior face 100. In the winding procedure being discussed, the oxygenator exterior face 100 is covered, except for the gap spacing 124 (FIG. 4B) between adjacent fibers 110. Fibers of the ribbon 140 laid down at a later traverse of the guide head 132 will be in radial registry with the fibers 110 laid down during an earlier traverse of the guide head 132 as described in the '247 patent.

With embodiments in which the depth filter region 36 (FIG. 3A) is formed by winding the fibers 110 onto the oxygenator region 34 as described above, the ratio of the mounting member 130 rotational speed relative to the traverse motion of the guide head 132 can be adjusted incrementally during the winding operation, thereby adjusting a wind angle of the fiber ribbon 140. With this approach, a packing fraction of the fibers 110 along radial a thickness of the depth filter region 36 is affected to provide a radially increasing packing fraction. Alternatively, or in addition, a tension of the fibers 110 can be regulated during the winding process. In particular, an optional roller 142 can be employed to apply tension to the ribbon 140. The roller 142 may rotate in response to the fiber ribbon 140 moving against it or may be driven so that its rotation matches the speed of the ribbon 140. Where the tension of the fibers 110 is increased during winding, an increasing packing fraction is obtained in a radially outward direction; thus, a force of the roller 142 against the fibers 110 can be increased to increase the resultant packing fraction. As a further alternative, a spacing between two (or more) fibers being simultaneously wound may be decreased during the winding operation, either incrementally or continuously, to increase packing fractions in a radially outward direction as described, for example, in the '619 patent. In other embodiments, the packing fraction can be constant or decreasing in the radially outward direction. In yet other embodiments, the fibers 110 can be wound on a more individual basis (e.g., the continuous ribbon 140 technique described above need not be employed).

In some embodiments, the winding apparatus described above is employed to form the oxygenator region 34 about the internal core 38. For example, the internal core 38 is initially assembled to the rotating mounting member 130, and the guide head 132 employed to apply a ribbon of the fibers 102 (FIG. 3B) onto the internal core 38. Following formation of the oxygenator region 34, the winding process continues, with the fibers 102 now serving as the fibers 110 of the depth filter region 36. It has surprisingly and unexpectedly been found that a fiber bundle appropriate for extracorporeal circuit blood oxygenating and arterial filtering operations can be formed by winding oxygenator fibers beyond the normal bundle outer diameter (otherwise utilized for conventional oxygenator functions) to an increased bundle outer diameter (e.g., the difference between the conventional oxygenator fiber bundle outer diameter and the elevated outer diameter providing desired arterial filtration properties). Alternatively, following formation of the oxygenator region 34, the fibers 102 are removed from the fiber guides (e.g., withdrawn from the tubes carried by the guide head 132), and replaced with the filter fibers 110 as described above. Thus, the depth filter region 36 can optionally be formed over the oxygenator region 34 immediately after applying the fibers 102 to the internal core 38 and without removing the so-formed oxygenator region 34 from the winding apparatus.

Figure 6B:
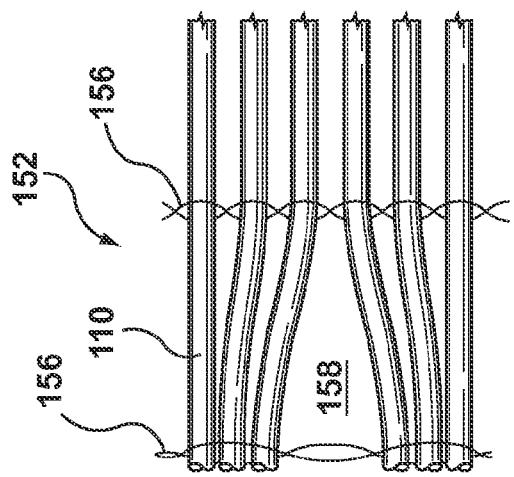
FIG. 6B is an enlarged view of a portion of the fiber bundle of FIG. 6A.
Figure 6A:
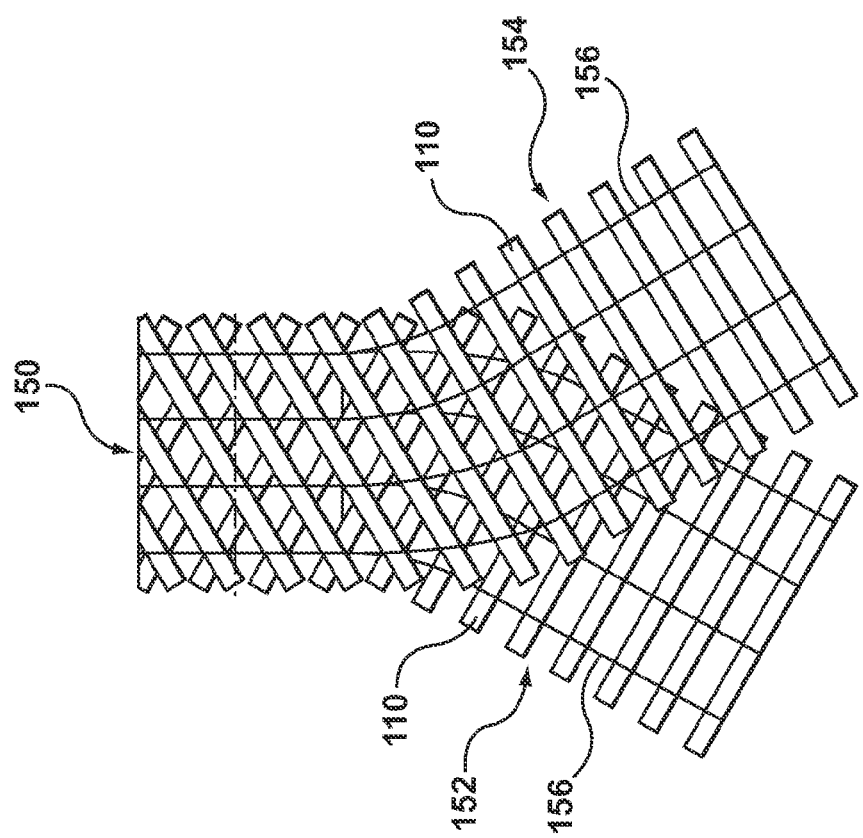
FIG. 6A is a simplified schematic illustration of another embodiment fiber bundle useful with the devices of FIGS. 2A-2D.

While the fiber bundle 33 has been described as being wound directly onto the core 38, other constructions are also acceptable. For example, the fiber bundle 33 can be formed or provided apart from the core 38 (or the depth filter region 36 formed or provided apart from the oxygenator region 34) as a filament mat, comprising two or more plies. U.S. Pat. No. 4,940,617 describes two-ply (or multi-ply) mats having parallel fibers interconnected by cross-stitching where the fibers in one ply form an angle relative to the fibers in an adjacent ply or layer. The '617 patent also shows the construction of bundles by winding such mats onto a core. Column 3, line 26 through column 14, line 67, including the figures referenced therein, contain the disclosure of such mats and bundles and the teachings of which are incorporated herein by reference, it being understood that the fibers 110 of the present disclosure could be used as the fibers of the '617 patent. In general terms, and as shown in FIG. 6A, a mat 150 useful as the fiber bundle 33 (or as the depth filter region 36 (FIG. 2A)) in accordance with the present disclosure consists of the fibers 110 combined into groups or plies 152, 154 by special disposition of inserted transverse fibers 156 or the like. In some constructions, and as shown in FIG. 6B for one of the plies 152, an interval between some of the fibers 110 can vary from the interval between others of the fibers 110. A gap 158, formed by this disposition of fiber ends, between the fiber groups, permits better penetration of the medium flowing around the filaments 110 in the resultant mat 150. Returning to FIG. 6A, the additional transverse fibers 154 or the like, inserted in the middle of the fibers 110, are disposed such that they hold the fibers 110 at a regular, essentially identical interval to each other. Regardless of an exact construction, and with cross-reference to FIG. 3A, the mat 150 is rolled or wrapped about the core 38 (or the exterior face 100 of the oxygenator region 34), and forms the depth filter region 36 of the fiber bundle 33 as having at least the first and second layers of cross-wound hollow fibers as described above.

Figure 7:
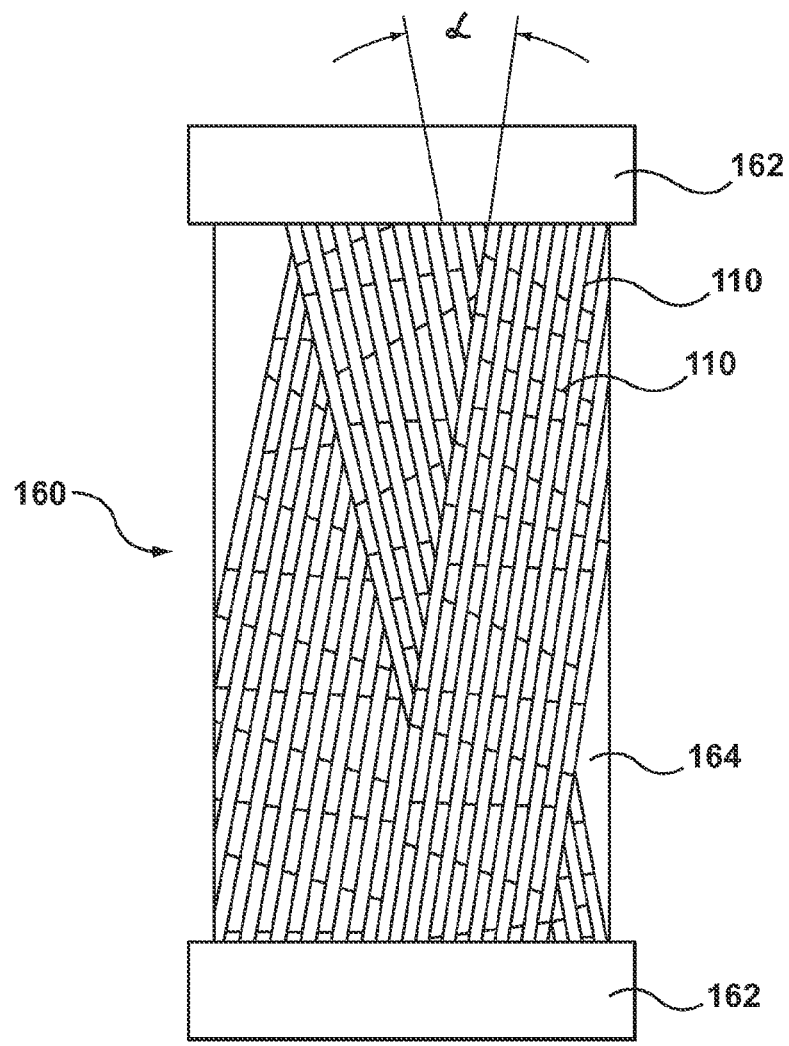
FIG. 7 is a simplified schematic illustration of a double weft tape useful as the fiber bundle of the devices of FIGS. 2A-2D.

In yet another acceptable embodiment, the fiber bundle 33 (or at least the depth filter region 36) is provided as a woven fiber double weft tape as described, for example, in U.S. Pat. No. 5,141,031, the entire teachings of which are incorporated herein by reference. In general terms, and as shown in FIG. 7, a double weft tape 160 including a plurality of the fibers 110 are embedded in head plates 162. Typically, the fiber ends are embedded by spinning them into a curable potting compound. Regardless, the double weft tape 160 provides various fiber tapes arranged in layers around a core 164 (e.g., the core 38 (FIG. 3A)) in such a way that the fibers 110 of adjacent layers form layers with an angle α that is not greater than 30° in some embodiments. The double weft tape 160 is akin to the two-ply mat 150 (FIG. 6A) described above, but typically exhibits a more narrow width. The tape 160 can be wrapped or wound about the core 38 (or about the oxygenator exterior face 100 (FIG. 3A)) to form the depth filter region 36 as described above.

Returning to FIGS. 4A and 4B, regardless of an exact construction of the fiber bundle 33, the first and second filter layers 120, 122 of level wound fibers establish a tortuous radial flow path for blood flow through the depth filter region 36. Thus, the depth filter region 36 is markedly different from the screen or mesh construction associated with conventional arterial filters. In other words, the radial flow paths (i.e., gap spacings) between the fibers 110 of the first layer 120 are not radially aligned with those of the second layer 122, thus defining a "depth" to the depth filter region 36. In contrast, with screen or mesh filters, the flow path spacing are radially open or "linear" through a thickness of the material. The minimum gap spacings 124 between the fibers 110 and the number of filter layers are two of the factors that determine the efficiency of the depth filter region 36 for a given size of microemboli. Further, the gap spacings 124 between the fibers 110, the outer diameter of the fibers 110, and the crossing angle of the fibers 110 determine a percentage of open area of the depth filter 36. By varying the packing fraction, for example, the minimum gap spacings 124 between the fibers 110 can be reduced (as compared to the minimum gap spacings 104 (FIG. 3C) between the fibers 102 of the oxygenator region 34) without increasing the shear to which the blood flow is exposed. In some embodiments, the depth filter region 36 or the fiber bundle 33 as a whole is configured to filter or remove microemboli as understood in the art, for example particulate microemboli as small as 15 micron, and gaseous microemboli (i.e., bubbles) on the order of 250 microns or less. With embodiments in which the fibers 110 are microporous gas conducting hollow fibers, a pressure drop across the depth filter region 36 will provide a favorable pressure gradient to drive gaseous microemboli through the pores and into the lumens of the fibers 110. The gas from the so-captured gaseous microemboli can be vented to the atmosphere through the gas outlet 68 (FIG. 2A) associated with the fiber bundle 33, or to a separate manifold.

Figure 8:
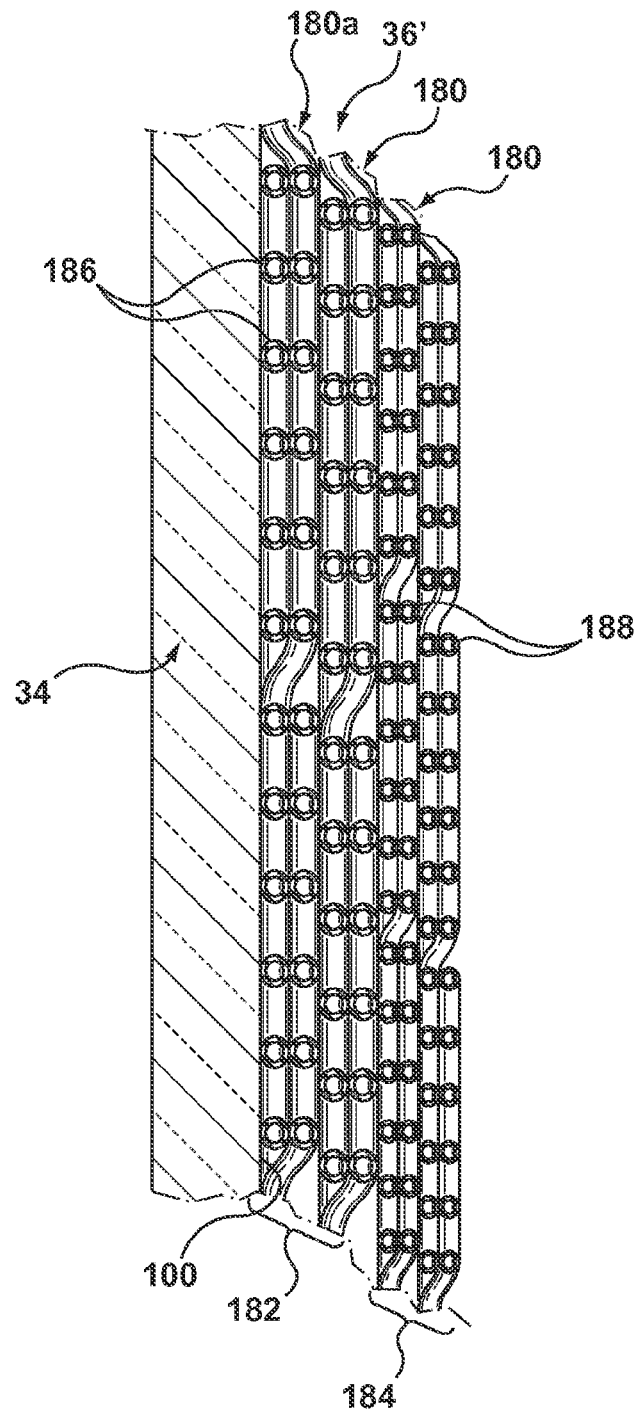
FIG. 8 is a cross-sectional, greatly magnified view of an alternative fiber bundle useful with the devices of FIGS. 2A-2D.

While the depth filter region 36 has been described as utilizing relatively uniform filaments across a radial thickness of the depth filter 36, in other constructions, variations in the depth filter fibers 110 can be incorporated. For example, FIG. 8, illustrates, in simplified form, a portion of an alternative depth filter region 36' in accordance with the present disclosure. The depth filter region 36' is akin to previous embodiments, and includes a plurality of level wound fibers combining to define two or more filter layers 180. As a point of reference, the inner most layer 180a is placed in direct physical contact with the exterior face 100 of the oxygenator region 34 (illustrated schematically) upon final assembly. Various differences are incorporated into one or more of the layers 180 to create two (or more) filtering zones 182, 184 exhibiting different filtration characteristics or properties. For example, fibers 186 of the first zone 182 can be hollow, whereas fibers 188 of the second zone 184 are solid (or vice-versa); as a result, the first zone 182 more readily filters or removes gaseous microemboli, whereas the second zone 184 more actively filters particulate microemboli. Other differences, such as fiber materials, minimum gap spacings, packing fraction, etc., can alternatively or additionally be incorporated in the zones 182, 184 to provide desired dual functioning filtration.

Returning to FIG. 3A, although in certain respects the level cross-woven fiber layers of the depth filter region 36 are akin to the oxygenator region 34, one or more structural differences can exist in some embodiments between the depth filter region 36 and the oxygenator region 34. In general terms, these differences are uniquely selected to promote functioning of the oxygenator region 34 primarily to oxygenate (and remove carbon dioxide from) blood flow, whereas the depth filter region 36 primarily removes or filters gaseous and particulate microemboli. For example, in some embodiments, the minimum gap spacing between axially adjacent ones of the oxygenator region fibers 102 is greater than the minimum gap spacing between axially adjacent ones of the depth filter fibers 110 (e.g., the minimum gap spacing between axially adjacent ones of the oxygenator bundle fibers 102 is in the range of 75-150 microns, whereas the minimum gap spacing between axially adjacent ones of the depth filter fibers 110 is in the range of 40-75 microns). In yet other embodiments, a packing fraction of the depth filter region 36 is higher than the packing fraction of the oxygenator region 34. Alternatively, or in addition, a wind angle associated with the fibers 102 of the oxygenator region 34 differs from the wind angle associated with the filaments 110 of the depth filter region 36. In some constructions, two or more of the above-described differences are incorporated into the depth filter region 36 and the oxygenator region 34. Alternatively, other differences can be employed. The plastic resin of the depth filter fibers 110 can differ from the plastic resin of the oxygenator region fibers 102 (e.g., the depth filter fibers 110 are formed of polyester, poly methyl pentene, or silicone, whereas the oxygenator region fibers 102 are formed of polypropylene). In yet other embodiments, an outer diameter of the oxygenator region fibers 102 is greater than an outer diameter of the depth filter filaments 110 (e.g., the oxygenator region fibers 102 have an average outer diameter in the range of 200-300 microns, whereas the depth filter fibers 110 have an average outer diameter in the range of 100-250 microns).

Figure 9:
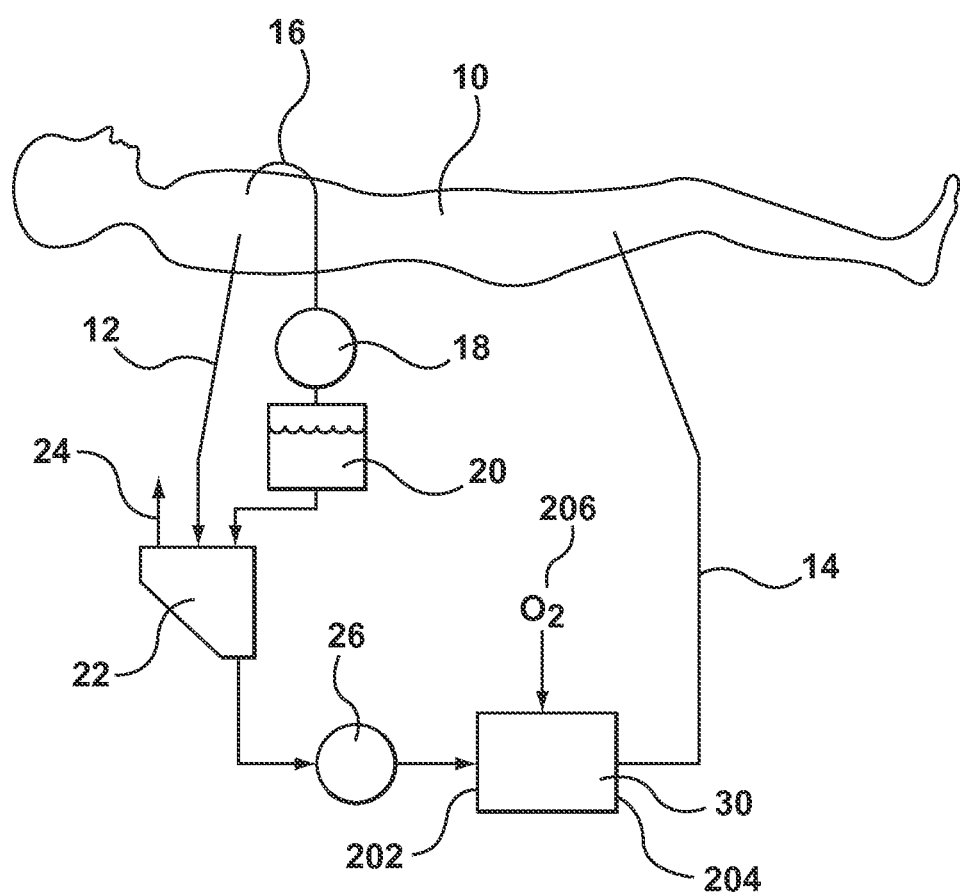
FIG. 9 is a schematic diagram of an extracorporeal blood circuit incorporating the devices of FIGS. 2A-2D in accordance with principles of the present disclosure.

The combination oxygenator and arterial filter device 30 can be incorporated into an extracorporeal blood circuit 200 as shown in FIG. 9. In general terms, the extracorporeal blood circuit 200 can be akin to any extracorporeal blood circuit commonly employed, and generally includes the venous return line 12, the cardiotomy pump and reservoir 20, the venous blood reservoir 22, and the arterial line 14 as described above. The combination oxygenator and arterial filter device 30 is fluidly connected to the venous line 12, for example via an inlet side 202. An outlet side 204 of the device 30 is fluidly connected to the arterial line 14. A source of oxygenating gas 206 is fluidly connected to the device 30, establishing an oxygenating gas flow path to at least the hollow fibers 102 (FIG. 3C) of the oxygenator region 34 (FIG. 3A). Additional components can be interposed within the circuit 200. However, in accordance with embodiments of the present disclosure, the device 30 provides necessary arterial filtration, such that a separate or additional arterial filter is not included between the device 30 and the arterial line 14. As compared to conventional extracorporeal blood circuit configurations, then, an overall prime volume is reduced with use of the device 30. The extracorporeal blood circuit 200 is thus simplified as one less component need be fluidly connected into the circuit 200.

Examples

The following examples and comparative examples further describe the combination oxygenator and arterial filter devices of the present disclosure. The examples are provided for exemplary purposes to facilitate an understanding of the present disclosure, and should not be construed to limit the disclosure to the examples.

Example combination oxygenator and arterial filter devices (Examples 1-6) were constructed by forming a depth filter directly over the oxygenator bundle of a commercially available oxygenator (an Affinity® NT Oxygenator available from Medtronic, Inc., of Minneapolis, Minn., the fibers of which were coated with a Trillium® Biosurface available from BioInteractions, Ltd., UK). The integrated arterial depth filter was formed by continuing the spiral or cross-winding of the oxygenator fibers in predetermined fashions to establish two or more filter layers of level cross-wound fibers, including a designated gap spacing between axially adjacent fibers. The fiber outer diameter, number of filter layers, and gap spacing for each of Examples 1-6 are set forth in the Table 1 below.

The filtration efficiency of the combination oxygenator and arterial filter devices of Examples 1-6 was tested by flowing a particle-laden fluid through the device, and determining the percentage of particles captured or retained by the device. The particles were latex microspheres, and batches of differently-sized particles were employed with tests for each sample. For each test, the difference between the number of the particles introduced to the device and number particles exiting the device were recorded and used to determine filtration efficiency. The particle size for each test is shown in Table 1 below, along with the determined filtration efficiency.

To evaluate the filtration efficiency performance of the example combination oxygenator and arterial filter devices, commercially available arterial filters and commercially available oxygenators were subjected to the tests descried above, and the results recorded. In particular, Comparative Examples 1 and 2 were commercially available arterial filters (Affinity® Arterial Filter (38 micron filament gap)) coated with Trillium® Biosurface. Comparative Examples 3 and 4 were commercially available arterial filters (Affinity® Arterial Filter) coated with Carmeda® Biosurface (available from Carmeda AB of Sweden). Comparative Examples 5 and 6 were commercially available oxygenators (Affinity® NT Oxygenator available from Medtronic, Inc., of Minneapolis, Minn.) coated with Carmeda® Biosurface. Comparative Examples 7 and 8 were commercially available oxygenators (Affinity® NT Oxygenator) coated with Trillium® Biosurface. The test results are provided in Table 1 below.

TABLE 1

| | Filtration Efficiency | | | | Integrated Arterial Filter | | |
| --- | --- | --- | --- | --- | --- | --- | --- |
| Sample | 20 μm particles | 45 μm particles | 65 μm particles | 90 μm particles | Fiber OD (microns) | Gap (microns) | # Crossing Layers |
| E1 | 34.9% | 94.6% | 99.1% | 100.0% | 200 | 58 | 2 |
| E2 | 56.2% | 98.8% | 100.0% | 100.0% | 130 | 58 | 6 |
| E3 | 57.9% | 97.2% | 99.9% | 99.9% | 130 | 58 | 6 |
| E4 | 41.4% | 94.8% | 99.4% | 100.0% | 200 | 58 | 2 |
| E5 | 19.2% | 95.4% | 99.7% | 99.9% | 130 | 58 | 2 |
| E6 | 38.1% | 92.8% | 99.1% | 100.0% | 130 | 51/51 | 2 |
| CE1 | 11.7% | 100.0% | N/A | N/A | NA | 38 | NA |
| CE2 | 35.0% | 99.8% | N/A | N/A | NA | 38 | NA |
| CE3 | 37.8% | 99.8% | N/A | N/A | NA | 38 | NA |
| CE4 | 12.7% | 100.0% | N/A | N/A | NA | 38 | NA |
| CE5 | 54.5% | 95.9% | 99.7% | 100.0% | NA | NA | NA |
| CE6 | 45.4% | 94.6% | 99.1% | 99.2% | NA | NA | NA |
| CE7 | 41.2% | 92.6% | 99.1% | 100.0% | NA | NA | NA |
| CE8 | 17.6% | 90.8% | 98.9% | 100.0% | NA | NA | NA |

Additional example combination oxygenator and arterial filter devices (Examples 7-11) in accordance with the present disclosure were constructed by forming an enlarged fiber bundle of 300 micron hollow porous fibers in a manner akin to FIG. 2D. The enlarged diameter bundles of Examples 7-11 were premised upon the fiber bundle of an oxygenator device available under the trade name Pixie™ Oxygenator available from Medtronic, Inc. of Minneapolis, Minn. In particular, the fiber bundles of Examples 7-11 represented "upsized" versions of the conventional Pixie™ oxygenator bundle. The upsized fiber bundles of Examples 7-11 were wound to have an increasing packing fraction along the added bundle diameter, including a decreasing gap spacing as compared to the minimum gap spacing of the normal Pixie™ bundle. Examples 7-11 were subjected to the filtration efficiency testing described above, the results of which are reported in Table 2 below.

To evaluate the filtration efficiency performance of the combination oxygenator and arterial filter devices of Examples 7-11, commercially available arterial filters and commercially available oxygenators were subjected to the tests descried above, and the results recorded. In particular, Comparative Examples 9 and 10 were commercially available arterial filters (Affinity® Arterial Filter (38 micron fiber gap)) coated with Trillium® Biosurface. Comparative Examples 11 and 12 were commercially available oxygenators (Affinity® NT Oxygenator available from Medtronic, Inc., of Minneapolis, Minn.) coated with Trillium® Biosurface. The test results are provided in the Table 2 below.

TABLE 2

| | Filtration Efficiency | | | |
| --- | --- | --- | --- | --- |
| Sample | 20 μm Particles | 45 μm particles | 65 μm particles | 90 μm particles |
| E 7 | 64.9% | 96.8% | 98.0% | 99.1% |
| E 8 | 62.2% | 96.7% | 98.3% | 98.8% |
| E 9 | 71.4% | 98.2% | 99.0% | 99.3% |
| E 10 | 67.1% | 97.0% | 97.6% | 98.7% |
| E 11 | 61.2% | 97.2% | 98.3% | 99.1% |
| CE 9 | 14.0% | 99.5% | N/A | N/A |
| CE 10 | 35.3% | 99.7% | N/A | N/A |

TABLE 2-continued

| | Filtration Efficiency | | | |
|---|---|---|---|---|
| Sample | 20 μm Particles | 45 μm particles | 65 μm particles | 90 μm particles |
| CE 11 | 51.3% | 90.1% | 92.1% | 96.6% |
| CE 12 | 45.6% | 88.3% | 89.6% | 95.3% |

The test results reveal that the combination oxygenator and arterial filter devices of the present disclosure were highly beneficial in filtration efficiency as compared to separate, standalone oxygenator and arterial filter products. Surprisingly, exemplary fiber bundle embodiments of the present disclosure in which the fiber bundle depth filter region is formed by continued winding of the hollow microporous fibers of the oxygenator region, including a decreased minimum gap spacing along the depth filter region as compared to the oxygenator region, exhibited highly beneficial filtration efficiencies. For example, fiber bundles of the present disclosure useful with a combination oxygenator and arterial filter device provide oxygenation properties necessary for extracorporeal blood circuit oxygenation functions and exhibit filtration efficiencies in filtering particles having a particle size of about 45 microns (+/−5 microns) of not less than 92%, alternatively not less than 95%; in other embodiments, the fiber bundles have a filtration efficiency of not less than 94%, alternatively not less than 97% in filtering particles having a particle size of about 65 microns (+/−5 microns); in yet other embodiments, the fiber bundles have a filtration efficiency of not less than 55%, alternatively not less than 60% in filtering particles having a particle size of about 20 microns (+/−5 microns).

Although the present disclosure has been described with reference to preferred embodiments, workers skilled in the art will recognize that changes can be made in form and detail without departing from the spirit and scope of the present disclosure.

What is claimed is:

1. A combination oxygenator and arterial filter device for treating blood in an extracorporeal blood circuit, the device comprising:
    a housing;
    a core maintained within the housing and defining a central longitudinal axis; and
    a fiber bundle disposed within the housing, the fiber bundle formed by a plurality of hollow microporous fibers continuously helically wound about the core to generate a plurality of layers, each layer being composed of level wound fibers and each successive layer being radially outward of an immediately preceding layer relative to the central longitudinal axis;
    wherein the layers of the fiber bundle combine to define an oxygenator region and a depth filter region, the depth filter region being radially outward of the oxygenator region;
    and further wherein:
    a minimum gap spacing between axially adjacent fibers of the oxygenator region layers is greater than a minimum gap spacing between axially adjacent fibers of the depth filter region layers,
    the fiber bundle exhibits a filtration efficiency of not less than 92% in filtering particles having a particle size of about 45 microns.

2. The device of claim 1, wherein the filtration efficiency of the fiber bundle is not less than 95% in filtering particles having a particle size of about 45 microns.

3. The device of claim 1, wherein the fiber bundle exhibits a filtration efficiency of not less than 94% in filtering particles having a particle size of about 65 microns.

4. The device of claim 3, wherein the filtration efficiency of the fiber bundle is not less than 97% in filtering particles having a particle size of about 65 microns.

5. The device of claim 1, wherein the fiber bundle exhibits a filtration efficiency of not less than 55% in filtering particles having a particle size of about 20 microns.

6. The device of claim 5, wherein the filtration efficiency of the fiber bundle is not less than 60% in filtering particles having a particle size of about 20 microns.

7. The device of claim 1, wherein the filtration efficiency of not less than 92% is for a liquid carrying the particles and dispensed through the device.

8. The device of claim 1, wherein a packing fraction of the depth filter region is greater than the packing fraction of the oxygenator region.

9. The device of claim 1, wherein the minimum gap spacing between axially adjacent fibers of a radially inward layer of the depth filter region is greater than the minimum gap spacing between axially adjacent fibers of a radially outward layer of the depth filter region.

10. The device of claim 1, wherein the minimum gap spacing between axially adjacent fibers of the oxygenator region layers is in the range of 75-150 microns, and the minimum gap spacing between axially adjacent fibers of the depth filter region layers is in the range of 40-75 microns.

11. The device of claim 1, wherein the fibers have an outer diameter of approximately 300 microns.

12. The device of claim 1, wherein the device further includes a heat exchanger bundle formed between the fiber bundle and the core.

13. The device of claim 12, wherein the fiber bundle has an outer diameter of approximately 3.5 inches and an inner diameter of approximately 2.0 inches.

14. The device of claim 1, wherein the housing includes an inlet and an outlet, and defines a blood flow path from the inlet, radially through the oxygenator region, radially through the depth filter region, and to the outlet.

15. The device of claim 14, wherein the fiber bundle establishes a radially tortuous blood flow path.

16. The device of claim 1, wherein the oxygenator regions is configured to primarily remove carbon dioxide from and add oxygen to venous blood flowing through the fiber bundle, and the depth filter region is configured to primarily remove particulate and gaseous microemboli from blood flowing through the fiber bundle.

17. The device of claim 1, wherein the layers are each composed of level cross-wound fibers.

18. An extracorporeal blood circuit comprising:
    a venous line for receiving venous blood from a patient;
    an arterial line for delivering blood to a patient; and
    a combination oxygenator and arterial filter device having an inlet side fluidly connected to the venous line and an outlet side fluidly connected to the arterial line, the device comprising:
    a housing,
    a core maintained within the housing and defining a central longitudinal axis,
    a fiber bundle disposed within the housing, the fiber bundle formed by a plurality of hollow microporous fibers continuously helically wound about the core to generate a plurality of layers, each layer being composed of level wound fibers and each successive layer being radially outward of an immediately preceding layer relative to the central longitudinal axis, wherein the layers of the fiber bundle combine to define an oxygenator region and a depth filter region, the depth filter region being radially outward of the oxygenator region,
and further wherein:
a minimum gap spacing between axially adjacent fibers of the oxygenator region layers is greater than a minimum gap spacing between axially adjacent fibers of the depth filter region layers,
the fiber bundle exhibits a filtration efficiency of not less than 92% in filtering particles having a particle size of about 45 microns.

19. The extracorporeal blood circuit of claim 18, wherein the circuit is characterized by the absence of an additional arterial filter between the device and the arterial line.

* * * * *